(12) United States Patent
Klug et al.

(10) Patent No.: US 6,884,409 B2
(45) Date of Patent: Apr. 26, 2005

(54) DEODORANTS AND ANTIPERSPIRANTS

(75) Inventors: Peter Klug, Grossostheim (DE); Norbert Rösch, Gersthofen (DE); Karl Werner Reiser, Garbsen (DE)

(73) Assignee: Clariant GmbH, Frankfurt (DE)

( * ) Notice: Subject to any disclaimer, the term of this patent is extended or adjusted under 35 U.S.C. 154(b) by 289 days.

(21) Appl. No.: 10/322,959

(22) Filed: Dec. 18, 2002

(65) Prior Publication Data

US 2003/0138389 A1 Jul. 24, 2003

(30) Foreign Application Priority Data

Dec. 21, 2001 (DE) .......................... 101 63 242

(51) Int. Cl.$^7$ ............................ A61K 7/38; A61K 7/32; A61K 7/00
(52) U.S. Cl. ........................... 424/68; 424/65; 424/400; 424/401
(58) Field of Search ........................... 424/65, 68, 400, 424/401

(56) References Cited

U.S. PATENT DOCUMENTS 3,876,758 A * 4/1975 Beekman ..................... 424/47
5,908,616 A 6/1999 Parekh et al.

FOREIGN PATENT DOCUMENTS

| EP | 0 530 598 | 3/1993 |
| WO | WO 98/58625 | 12/1998 |
| WO | WO 00/71091 | 11/2000 |

OTHER PUBLICATIONS

English abstract for EP 0530598, Mar. 10, 1993.

* cited by examiner

Primary Examiner—Shelley A. Dodson
(74) Attorney, Agent, or Firm—Richard P. Silverman

(57) ABSTRACT

Deodorants and antiperspirants comprising aluminum chlorohydrates according to the formula I $$Al_2(OH)_nCl_z \qquad (I)$$

where n is a number between 4.5 and 5.1 and z is a number between 1.5 and 0.9 and n+z is always 6, with an iron content of less than 20 ppm, preferably less than 10 ppm, based on the dry substance.

5 Claims, No Drawings

DEODORANTS AND ANTIPERSPIRANTS

The present invention relates to antiperspirants and cosmetic deodorizing compositions comprising aluminum chlorohydrate with an iron content of less than 20 ppm, based on 100% of solid. The low-iron aluminum chlorohydrates are characterized by improved effectiveness in antiperspirant products.

The use of basic aluminum chlorides in deodorants and antiperspirants for reducing perspiration has been known for a long time.

Such basic aluminum chlorides can, as described in German patent 23 09 610, be prepared by reacting aluminum hydroxide with hydrochloric acid at temperatures between 70° C. and 140° C. or by a redox reaction of aluminum and aluminum chloride hydrate at temperatures around 90 to 100° C.

The macromolecular structure of the aluminum chlorohydrates is very complex and is composed of various cluster polyethers with varying molecular weights. It is known that the astringent effect of aluminum chlorohydrates with a relatively high proportion of clusters having relatively low molecular weights is more marked compared with high molecular weight cluster fractions. These so-called activated aluminum chlorohydrates are metastable and change their macrostructure depending on temperature, concentration of the solution and storage period.

The use of aluminum chlorohydrates as antiperspirant active ingredient in cosmetic formulations has been known for a long time and is well documented. The aluminum chlorohydrates suitable for cosmetic applications can, depending on the raw materials used, contain iron and other trace metals in amounts of from 40 ppm to 200 ppm, based on 100% of dry substance. Typical values for the aluminum chlorohydrates used currently are about 40–100 ppm, based on 100% of dry substance. This iron content originates essentially from the iron content of the starting aluminum hydroxide or aluminum metal. The commercial form of aluminum chlorohydrates used is generally a 50% aqueous solution, but also flakes, spray powders and ground powders.

Surprisingly, it has now been found that aluminum chlorohydrates have a significantly improved effect in an antiperspirant formulation if they have an iron content below 20 ppm, preferably below 10 ppm (based on 100% of dry substance). This effect is surprising since it was expected that a trace element would exhibit no decisive effect on the effect of the aluminum chlorohydrates.

The invention provides deodorants and antiperspirants comprising aluminum chlorohydrates according to the formula I $$Al_2(OH)_nCl_z \qquad (I)$$

where n is a number between 4.5 and 5.1 and z is a number between 1.5 and 0.9 and n+z is always 6, with an iron content of less than 20 ppm, preferably less than 10 ppm, based on the dry substance.

The high-purity aluminum chlorohydrates used according to the invention are obtained by bringing aqueous solutions of those aluminum chlorohydrates which contain an increased proportion of iron and other metals into contact with metallic aluminum, for example in the form of bars, chips or granules, at temperatures of from 70 to 140° C.

The proportion by weight of the aluminum chlorohydrates in the antiperspirants according to the invention is typically 0.01% by weight to 20% by weight, preferably 0.05% by weight to 15% by weight, particularly preferably 0.1 to 10% by weight, based on the finished composition and 100% of active substance, of aluminum chlorohydrate.

The antiperspirants according to the invention can be supplied in various forms, such as gels, sticks, creams, sprays, powders, powder sprays, and can comprise all the customary constituents, such as further astringents, antimicrobial active ingredients, gelling agents, alcohols, oils, waxes, emulsifiers and coemulsifiers, superfatting agents, moisturizing agents, stabilizers, biogenic active ingredients (local anesthetic, antibiotics, antiphlogistics, antiallergics, corticosteroids, sebostatics), vitamins, panthenol, allantoin, plant extracts, for example aloe vera and proteins, glycerol, preservatives, pearlescent agents, dyes and fragrances, solvents, hydrotropic agents, enzymes, carrier substances, for example phyllosilicates, pyrogenic silica, electrolyte salts, such as KCl, NaCl, complexing agents, antioxidants and UV light protection filters.

Suitable further astringents are oxides, preferably magnesium oxide, aluminum oxide, titanium dioxide, zirconium dioxide and zinc oxide, oxide hydrates, preferably aluminum oxide hydrate (boehmite) and hydroxides, preferably of calcium, magnesium, aluminum, titanium, zirconium or zinc.

In addition to the aluminum chlorohydrates, the antiperspirants according to the invention advantageously comprise antimicrobial active ingredients which suppress the perspiration-decomposing microorganisms or the perspiration-decomposing esterase enzyme. Preferably suitable antimicrobial active ingredients are cetyltrimethylammonium chloride, cetylpyridinium chloride, benzethonium chloride, diisobutylethoxyethyldimethylbenzylammonium chloride, sodium N-laurylsarcosinate, sodium N-palmethylsarcosinate, lauroylsarcosine, N-myristoylglycine, potassium N-laurylsarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, for example L-lysine hexadecylamide, heavy metal citrate salts, salicylates, piroctone, in particular zinc salts, pyrithiones and heavy metal salts thereof, in particular zinc pyropyrithione, zinc phenol sulfate, farnesol and combinations of these active substances.

The compositions according to the invention comprise the antimicrobial agents preferably in amounts up to 50% by weight, particularly preferably 0.01 to 10% by weight, especially preferably 0.1 to 5% by weight.

In addition, the compositions according to the invention preferably comprising gelling agents. Suitable gelling agents are all surface-active substances which, dissolved in the liquid phase, form a network structure and thus solidify the liquid phase. Suitable gelling agents are mentioned, for example, in WO 98/58625.

Preferred gelling agents are metal salts of fatty acids, preferably having 12 to 22 carbon atoms, for example sodium stearate, sodium palmitate, sodium laurate, sodium arachidate, sodium behenate, potassium stearate, potassium palmitate, sodium myristate, potassium palmitate, aluminum monostearate, hydroxy fatty acids, for example 12-hydroxystearic acid, -lauryl-, 16-hydroxyhexadecanoic acid; fatty acid amides; fatty acid alkanolamides; dibenzal sorbitol and alcohol-soluble polyamides and polyacrylamides or mixtures thereof.

In addition, the compositions according to the invention can also comprise gelling agents in the form of alkylsilicone waxes. Suitable waxes are, for example, $C_{20-24}$- alkyldimethicones (SilCare Silicone 41 M70), $C_{24}$–$C_{28}$-alkyldimethicones (SilCare Silicone 41 M80), $C_{20-24}$-alkylmethicones (SilCare Silicone 41 M40), $C_{24-28}$-alkylmethicones (SilCare Silicone 41 M50) and $C_{30-45}$-alkylmethicones. The compositions according to the invention preferably comprise 0.01 to 20% by weight, particularly preferably 0.1 to 10% by weight, especially preferably 1 to 8% by weight and very particularly preferably 3 to 7% by weight, of gelling agents.

In a further preferred embodiment, the compositions according to the invention comprise additional alcohols. Preferred alcohols are alkoxylated alcohols having preferably 1 to 80, particularly preferably 3 to 20, alkoxy groups and at least one free hydroxyl group.

Particular preference is given to ethanol, propanol, isopropanol, n-butanol, i-butanol, t-butanol, glycerol, diethylene glycol, triethylene glycol, dipropylene glycol, tripropylene glycol, liquid polypropylene-polyethylene glycol copolymers, tetrapropylene glycol, tetraethylene glycol, dibutylene glycol, trimethylene glycol, diethylene glycol monoethyl ether, PEG-8, 1,3-butanediol, 1,4-butanediol, glycerol propoxylate, propylene glycol, hexylene glycol, 1,2-hexanediol, 1,3-butylene glycol, 1,2,6-trihydroxyhexane and 1,2,3-trihydroxyhexane. Further preferred alcohols are polyethylene glycols with a relative molecular mass below 2000. In particular, preference is given to using polyethylene glycol with a relative molecular mass between 200 and 600 in amounts up to 45% by weight and of polyethylene glycol with a relative molecular mass between 400 and 600 in amounts of from 5 to 25% by weight. The compositions according to the invention preferably comprise 5 to 90% by weight, particularly preferably 5 to 80% by weight and especially preferably 20 to 60% by weight, of alcohol.

Fragrance or perfume oils which may be used are individual odorant compounds, e.g. the synthetic products of the ester, ether, aldehyde, ketone, alcohol and hydrocarbon type. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones, alpha-isomethylionone and methyl cedryl ketone, the alcohols include anethole, citronellol, eugenol, geraniol, linalool, phenylethyl alcohol and terpineol, the hydrocarbons include primarily the terpenes and balsams. Preference is given to using mixtures of different odorants which together produce a pleasing fragrance note.

Perfume oils can also comprise natural odorant mixtures, as are obtainable from vegetable or animal sources, e.g. pine oil, citrus oil, jasmine oil, lily oil, rose oil or ylang-ylang oil. Ethereal oils of low volatility, which are mostly used as aroma components, are also suitable as perfume oils, e.g. sage oil, camomile oil, oil of cloves, melissa oil, mint oil, cinnamon leaf oil, lime blossom oil, juniperberry oil, vetiver oil, olibanum oil, galbanum oil and ladanum oil.

The compositions according to the invention can comprise, as further auxiliaries and additives, oil bodies, emulsifiers and coemulsifiers, superfatting agents, moisturizing agents, stabilizers, biogenic active ingredients (local anesthetics, antibiotics, antiphlogistics, antiallergics, corticosteroids, sebostatics), vitamins, panthenol, allantoin, plant extracts, for example aloe vera and proteins, glycerol, preservatives, pearlescent agents, dyes and fragrances, solvents, hydrotropic agents, enzymes, carrier substances, for example phyllosilicates, pyrogenic silica, electrolyte salts, such as KCl, NaCl, complexing agents, antioxidants and UV light protection filters.

Oil body is to be understood as meaning any fatty substance which is liquid at room temperature (25° C.).

The fatty phase can comprise one or more oils which are preferably chosen from the following oils:

a) silicone oils, volatile or nonvolatile, linear, branched or ring-shaped, possibly organically modified, phenylsilicones, silicone resins and gums which are solid or liquid at room temperature, b) mineral oils, such as paraffin or vaseline oil c) oils of animal origin, such as perhydrosqualene or lanolin;

d) oils of vegetable origin, such as liquid triglycerides, e.g. sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's smock oil, castor oil, triglycerides of caprylic/capric acids, olive oil, groundnut oil, rapeseed oil and coconut oil;

e) synthetic oils, such as purcellin oil, isoparaffins, linear and/or branched fatty alcohols and fatty acid esters, preferably Guerbet alcohols having 6 to 18, preferably 8 to 10, carbon atoms; esters of linear ($C_6$–$C_{13}$)-fatty acids with linear ($C_6$–$C_{20}$)-fatty alcohols; esters of branched ($C_6$–$C_{13}$)-carboxylic acids with linear ($C_6$–$C_{20}$)-fatty alcohols, esters of linear ($C_6$–$C_{18}$)-fatty acids with branched alcohols, in particular 2-ethylhexanol; esters of linear and/or branched fatty acids with polyhydric alcohols (such as, for example, dimerdiol or trimerdiol) and/or Guerbet alcohols; triglycerides based on ($C_6$–$C_{10}$)-fatty acids;

f) esters, such as diioctyl adipates, diisopropyl dimer dilinoleate, propylene glycols/dicaprylates or waxes, such as beeswax, paraffin wax or microcrystalline waxes, optionally in combination with hydrophilic waxes, such as, for example, cetylstearyl alcohol, g) fluorinated and perfluorinated oils;

h) fluorinated silicone oils;

i) mixtures of the abovementioned substances.

Examples of suitable nonionogenic coemulsifiers are addition products of from 0 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan or sorbitol esters; ($C_{12}$–$C_{18}$)-fatty acid mono- and -diesters of addition products of from 0 to 30 mol of ethylene oxide onto glycerol; glycerol mono- and diesters and sorbitan mono- and diesters are saturated and unsaturated fatty acids having 6 to 22 carbon atoms and optionally ethylene oxide addition products thereof; addition products of from 15 to 60 mol of ethylene oxide onto castor oil and/or hydrogenated castor oil; polyol, and in particular polyglycerol, esters, such as, for example, polyglycerol polyricinoleate and polyglycerol poly-12-hydroxystearate. Mixtures of compounds from two or more of these classes of substance are likewise suitable.

Examples of suitable ionogenic coemulsifiers are anionic emulsifiers, such as mono-, di- or triphosphoric esters, but also cationic emulsifiers, such as mono-, di- and tri-alkyl quats and polymeric derivatives thereof.

Superfatting agents which can be used are substances such as, for example, polyethoxylated lanolin derivatives, lecithin derivatives, polyol fatty acid esters, monoglycerides and fatty acid alkanolamides, where the latter also serve as foam stabilizers. Available moisturizing substances are, for example, isopropyl palmitate, glycerol and/or sorbitol.

Stabilizers which can be used are metal salts of fatty acids, such as, for example, magnesium stearate, aluminum stearate and/or zinc stearate. Biogenic active ingredients are understood as meaning, for example, plant extracts and vitamin complexes.

The compositions according to the invention can be mixed with conventional ceramides, pseudoceramides, fatty acid N-alkylpolyhydroxyalkylamides, cholesterol, cholesterol fatty acid esters, fatty acids, triglycerides, cerebrosides, phospholipids and similar substances as care additive.

In order to adjust the rheological properties, a large number of different systems are given in the specialist literature. For example, cellulose ether and other cellulose derivatives (e.g. carboxymethylcellulose, hydroxyethylcellulose), gelatin, starch and starch derivatives, sodium alginates, fatty acid polyethylene glycol ester, agar agar, tragacanth or dextrins are known. The synthetic polymers used are various materials, such as, for example, polyvinyl alcohols, polyacrylamides, polyvinylamides, polysulfonic acids, polyacrylic acid, polyacrylic esters, polyvinylpyrrolidone, polyvinyl methyl ether, polyethylene oxides, copolymers of maleic anhydride and vinyl methyl ether, comb-like copolymers optionally containing grafted acryloyldimethyltaurate which, in the main or side chain, can additionally contain cationic charges or silicon, fluorine or phosphorus atoms, and various mixtures and copolymers of the abovementioned compounds, including their various salts and esters. These polymers may be crosslinked or uncrosslinked as desired.

Examples of suitable UV filters are 4-aminobenzoic acid; 3-(4'-trimethylammonium)benzylidenebornan-2-one methylsulfate; 3,3,5-trimethylcyclohexyl salicylate; 2-hydroxy-4-methoxybenzophenone; 2-phenylbenzimidazole-5-sulfonic acid and its potassium, sodium and triethanolamine salts; 3,3'-(1,4-phenylenedimethine)bis(7,7-dimethyl-2-oxobicyclo[2.2.1]heptane-1-methanesulfonic acid and its salts; 1-(4-tert-butylphenyl)-3-(4-methoxyphenyl)propane-3-(4'-sulfo)-benzylidenebornan-2-one and its salts; 2-ethylhexyl 2-cyano-3,3-diphenylacrylate; polymer of N-[2 (and 4)-(2-oxoborn-3-ylidenemethyl)benzyl]acrylamide; 2-ethylhexyl 4-methoxycin namate; ethoxylated ethyl 4-aminobenzoate; isoamyl 4-methoxycinnamate; 2,4,6-tris [p-(2-ethylhexyloxycarbonyl)anilino]-1,3,5-triazine; 2-(2H-benzotriazol-2-yl)-4-methyl-6-(2-methyl-3-(1,3,3,3-tetramethyl-1-(trimethylsilyloxy bis(2-ethylhexyl) 4,4'-[(6-[4-((1,1-dimethylethyl)aminocarbonyl)phenylamino]-1,3,5-triazin-2,4 bisbenzoate; 3-(4'-methylbenzylidene)-D,L-camphor; 3-benzylidenecamphor; 2-ethylhexyl salicylate; 2-ethylhexyl 4-dimethylaminobenzoate; hydroxy-4-methoxybenzophenone-5-sulfonic acid (sulisobenzonum) and the sodium salt and/or 4-isopropylbenzyl salicylate.

Available antioxidants are, for example, superoxide dismutase, tocopherol (vitamin E) and ascorbic acid (vitamin C). Suitable preservatives are, for example, phenoxyethanol, parabens, pentanediol or sorbic acid. Dyes which can be used are the substances approved and suitable for cosmetic purposes.

The deodorants and antiperspirants are lotions, creams, sticks (including multiphase sticks), sprays, roll-on preparations and powders. The compositions according to the invention have a pH of from 2 to 12, preferably 3–8, particularly preferably from 3.5 to 6.

To determine the antiperspirant effectiveness, 50% strength aluminum chlorohydrate solutions with a residual iron content of about 40 ppm (comparative example 1, Locron® L, Clariant, 80 ppm of iron based on 100% of dry substance) were compared in a comparison test with a 50% aluminum chlorohydrate solution with a residual iron content of 10 ppm based on 100% dry substance (example 1).

The test formulation used was an antiperspirant pump spray with the following formulation:

| A | Water | 40% |
|---|---|---|
| B | Aluminum chlorohydrate test product (50% strength solution in water) | 20% |
|   | Ethanol | 40% |

Preparation procedure: Add the components B to A and stir until homogeneous.

EXAMPLE 1

The following antiperspirant test was carried out in the armpit of 20 subjects:

Run-in phase:
During this, the subjects were allowed to wash for 10 days only with a mild syndet without perfume additive or antibacterial active ingredient and use no other cosmetics.

Blank test:
The armpit was firstly dried with cellulose, small silica gel bags were applied, and the perspiration secreted was determined gravimetrically over 24 hours by weighing the small silica gel bags.

Comparative experiment:
The effectiveness of the two antiperspirant active ingredients to be compared was then tested using the corresponding antiperspirant. For this, the pump spray was applied to the run-off point, left to act overnight, then the small silica bags were applied and the volume of perspiration was determined again over 24 hours from the weight increase in the small silica bags.

The perspiration reduction (in %, based on the blank experiment) after one application was:

Comparative example 1 (80 ppm of residual iron content): 21% Example 1 (10 ppm of residual iron content): 35%

EXAMPLE 2

An antiperspirant test was carried out with the above formulations from example 1 on the armpit of each of 20 subjects:

The intensity of the odor formation following application of the corresponding antiperspirant formulation was tested (sniff test):

Run-in phase:
For this, the subjects were conditioned as follows: Washing for 3 days only with a mild syndet without antibacterial active ingredient or perfume. During the study, only the unperfumed syndet was applied once daily.

Odor determinations were carried out a) prior to the first application of the experimental products 24 h after the last washing b) following application of the antiperspirant for 7 days, after 8 and 24 hours following application.

The odor formation was assessed by a panel of trained experts (3 people).

Evaluation was made on a scale from 0=no odor to 6=very strong odor.

Start value:
5.1 for both arms

| after 8 hours: | |
|---|---|
| Comparative example 1 (80 ppm of residual iron content): | 3.1 |
| Example 1 (10 ppm of residual iron content): | 2.5 |
| after 24 hours: | |
| Comparative example 1 (80 ppm of residual iron content): | 4.1 |
| Example 1 (10 ppm of residual iron content): | 3.2 |

The comparative examples show that the use of low-iron Locron grades with iron contents of <20 ppm lead to a marked and significant improvement in the antiperspirant effect.

The examples below describe further preparations according to the invention (all of the percentages given are % by weight).

EXAMPLE 3

Antiperspirant Cream

| | | |
|---|---|---|
| A | Cithrol GMS A/S | 15.0% |
| | Glyceryl stearate/PEG-100 stearate | |
| | Crodacol C90 EP | 5.0% |
| | Cetyl alcohol | |
| | Aristoflex HMB | 2.0% |
| B | Water | ad 100% |
| | Sorbitol (70% strength) | 3.0% |
| | Sorbitol | |
| | Aluminum chlorohydrate from Example 1 | 44.5% |
| C | Perfume oil | q.s |
| | Dyes | q.s |
| | Fragrances | q.s. |

Preparation:

I Heat A and B without Reach 501 to 70 to 75° C.

II Leave to cool with stirring

III Add Reach 501 at 50 to 55° C.

IV Add perfume oil at 40 to 45° C.

V Homogenize at 30 to 35° C.

EXAMPLE 4

Clear Antiperspirant Gel

| | | |
|---|---|---|
| A | Abil EM97 | 2.3% |
| | Dimethicone copolyl/cyclopentasiloxane | |
| | Abil B8839 | 6.9% |
| | Cyclopentasiloxane/cyclohexasiloxane | |
| | Abil K4 | 6.9% |
| | Cyclotetrasiloxane/cyclopentasiloxane | |
| | Aristoflex HMB | 1.5% |
| B | Aluminum chlorohydrate from Example 1 | 40.0% |
| | Propylene glycol | 25.0% |
| | Water, dist. | ad 100% |
| | Perfume oil | q.s. |

Preparation:

I Mix components A and B separately

II Slowly add phase B to phase A at room temperature with stirring.

III Homogenize

EXAMPLE 5

W/O Antiperspirant Cream

| | | |
|---|---|---|
| A | Abil EM90 | 2.0% |
| | Cetyldimethicone/copolyol | |
| | Abil B8839 | 20.0% |
| | Cyclopentasiloxane/cyclohexasiloxane | |
| | Aristoflex HMB | 2.0% |
| B | Aluminum chlorohydrate from Example 1 | 17.0% |
| | Water, dist. | ad 100% |
| | Perfume oil | q.s. |
| | Preservative | q.s. |

Preparation:

I Slowly add phase B to phase A at room temperature with stirring.

II Homogenize

EXAMPLE 6

O/W Antiperspirant Cream

| | | |
|---|---|---|
| A | Aristoflex HMB | 2.0% |
| | Arlamol ISML | 2.0% |
| | Isosorbide laurate | |
| | Dow Corning 245 fluid | 2.0% |
| | Cyclomethicone | |
| B | Water, dist. | ad 100% |
| | Aluminum chlorohydrate from Example 1 | 40.0% |
| | Preservative | q.s |
| | Perfume | q.s. |

Preparation

I Mix the components of A

II Add B to A with stirring

Aristoflex® HMB: Ammonium acrylyldimethyltaurate behenate-25 methacrylate copolymer

EXAMPLE 7

Roll-on Antiperspirant

| | | |
|---|---|---|
| A | Caprylyl trimethicone | 0.30% |
| | (SilCare ® Silicone 31 M 50) | |
| | Steareth-20 | 3.00% |
| | (GENAPOL ® HS 200) | |
| | Steareth-2 | 1.50% |
| | (GENAPOL ® HS 020) | |
| | Dicaprylyl ether | 2.00% |
| | (Cetiol ® OE) | |

-continued

|   | | |
|---|---|---|
|   | Coco caprylate/caprate (Cetiol ® LC) | 2.00% |
|   | Glycerol | 2.00% |
|   | Glyceryl stearate (Cutina ® GMS) | 2.00% |
|   | Octyldodecanol (Eutanol ® G) | 1.00% |
|   | Stearyl alcohol | 2.50% |
| B | Water | ad 100% |
|   | Aluminum chlorohydrate as in Example 1 | 10.00% |
|   | Avocado extract *Persea gratissima* | 0.30% |
| C | Perfume | 0.30% |

Preparation

A melt at about 70° C.;

B heat to about 70° C.;

Add components B to components A and stir until 35° C. has been reached; add component C at 35° C.

EXAMPLE 8

Antiperspirant Stick

|   | | |
|---|---|---|
| A | Phenyl trimethicone (SilCare ® Silicone 15 M 50) | 13.80% |
|   | Cetearyl alcohol | 19.30% |
|   | Cetiol CC (Dicaprylyl carbonate) | 13.80% |
|   | Stearic acid | 3.50% |
|   | PEG-40 hydrogenated castor oil (Emulsogen ® HCO 040) | 4.10% |
|   | PEG-8 distearate (Cithrol 4 DS) | 4.10% |
|   | Petrolatum | 6.90% |
| B | Aluminum chlorohydrate as in Example 1 Aluminum chlorohydrate | 34.50% |

Preparation

A melt at about 70° C.;

B heat to about 70° C.;

Add components B to components A with stirring; cool to about 50° C. and draw off.

What is claimed is:

1. A deodorant or antiperspirant comprising an aluminum chlorohydrate according to the formula I $$Al_2(OH)_nCl_z \qquad (I)$$

where n is a number between 4.5 and 5.1 and z is a number between 1.5 and 0.9 and n+z is always 6, wherein said aluminum chlorohydrate has an iron content of less than 20 ppm on a dry basis.

2. The deodorant or antiperspirant as claimed in claim 1, which comprises 0.01 to 20% by weight of the aluminum chlorohydrate.

3. The deodorant or antiperspirant as claimed in claim 1, which is in the form selected from the group consisting of a gel, stick, cream, spray, powder, and powder spray.

4. The deodorant or antiperspirant as claimed in claim 1, wherein the aluminum chlorohydrate has less than 10 ppm iron content on a dry basis.

5. A method for reducing perspiration on human skin comprising contacting the human skin with the deodorant or antiperspirant of claim 1.

* * * * *